Figure 1:
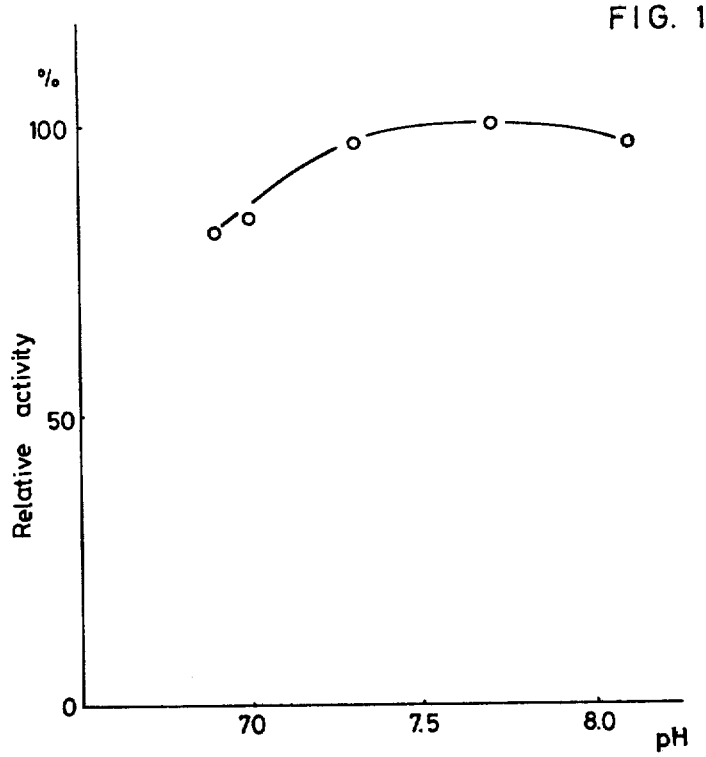

United States Patent [19]

Kikuchi et al.

[11] 4,371,620
[45] Feb. 1, 1983

[54] PROCESS FOR PRODUCING ACYL-COENZYME A OXIDASE

[75] Inventors: Toshiro Kikuchi; Masaru Ogawa; Makoto Ando, all of Tsuruga, Japan

[73] Assignee: Toyo Boseki Kabushiki Kaisha, Osaka, Japan

[21] Appl. No.: 362,133

[22] Filed: Mar. 26, 1982

Related U.S. Application Data

[63] Continuation of Ser. No. 127,536, Mar. 3, 1980, abandoned.

[30] Foreign Application Priority Data

Mar. 1, 1979 [JP] Japan .................................. 54-24232

[51] Int. Cl.³ .......................... C12N 9/02; C12Q 1/26; C12R 1/745
[52] U.S. Cl. .................................. 435/189; 435/25; 435/921
[58] Field of Search ............................. 435/189, 192

[56] References Cited

PUBLICATIONS

Stokes et al, Archives of Biochemistry and Biophysics, vol. 176, pp. 591-603, (1976).
Osumi et al, Biochemical and Biophysical Research Communications, vol. 83, No. 2, pp. 479-485, (1978).
Kawamoto et al, Eur. Journal Biochem., vol. 83, pp. 609-613, (1978).

*Primary Examiner*—Lionel M. Shapiro
*Attorney, Agent, or Firm*—Wenderoth, Lind & Ponack

[57] ABSTRACT

Novel acyl-coenzyme A oxidase is produced by cultivating an acyl-coenzyme A oxidase-producing microorganism belonging to the genus Candida in a nutrient medium, thereby accumulating an amount of acyl-coenzyme A oxidase in yeast cells and recovering the acyl-coenzyme A oxidase from said cells.

2 Claims, 5 Drawing Figures

PROCESS FOR PRODUCING ACYL-COENZYME A OXIDASE

This application is a continuation of application Ser. No. 127,536, filed Mar. 3, 1980, now abandoned.

The present invention relates to a novel acyl-coenzyme A oxidase (hereinafter referred to acyl-CoA oxidase) and production thereof. More particularly, the invention concerns a novel acyl-CoA oxidase which is produced by microorganism and which is capable of forming enoyl-coenzyme A and hydrogen peroxide from acyl-coenzyme A (hereinafter referred to acyl-CoA) in the presence of oxygen, and its production comprising cultivating the above-mentioned enzyme producing microorganism in a conventional nutrient medium, preferably containing n-alkanes or long-chain fatty acids, thereby accumulating a quantity of acyl-CoA oxidase in microorganism cells and extracting the enzyme from said cells.

Very little findings have been reported on acyl-CoA oxidase and there are only few publications making allusion to the possible existence of said enzyme.

For example, in Archives of Biochemistry and Biophysics 176, 591-603 (1976), a report entitled "A soluble acyl-coenzyme A oxidase from the yeast *Candida utilis*" by G. B. Stokes and P. K. Stumpf, it is stated that preparations of the upper layer of the high speed supernatant fraction obtained from disrupted *Candida utilis* cells were assayed for acyl-CoA oxidase activity. However, neither isolation nor purification of acyl-CoA oxidase has been carried out. Furthermore, there is indeed such statement that molecular oxygen was the only required cofactor for the crude enzyme contained in said supernatant fraction, but there includes no statement on the detection of hydrogen peroxide involved in that system. Thus, the publication fails to produce evidence of the existence of acyl-CoA oxidase.

In another publication of Eur. J. Biochem. 83, 609-613 (1978), a report entitled "Fatty acid β-oxidation system in microbodies of n-alkane-grown *Candida tropicalis*" by S. Kawamoto, C. Nozaki, A. Tanaka and S. Fukui, *Candida tropicalis* strain was cultivated in a medium containing n-alkane mixture ($C_{10}-C_{13}$) and the yeast cells were collected to prepare protoplast, whose roles in fatty acid β-oxidation system were studied. Thus, in that study, the use is described of subcellular particles, but not of enzyme itself. The presence of acyl-CoA oxidase has not been clarified yet.

On the other hand, as to acyl-CoA oxidase of rat liver, this has been isolated and highly purified and its activity has been thoroughly studied. For example, in Biochemical and Biophysical Research Communications, Vol. 83, No. 2, 1978, "Acyl-CoA oxidase of Rat liver" by T. Osumi and T. Hashimoto, there is such statement that the acyl-CoA oxidase of rat liver can catalyze the reaction of acyl-CoA with oxygen to produce trans-enoyl CoA and hydrogen peroxide.

From the foregoing, it is clear that in the art of microorganisms, the presence of acyl-CoA oxidase has remained unknown. No one can ever isolate this enzyme from microorganisms to study the enzymatic characteristics thereof.

The present inventors, having worked on this particular subject matter, have succeeded in obtaining an extract of soluble acyl-CoA oxidase by cultivating an acyl-coenzyme A oxidase producing microorganism in a nutrient medium, preferably containing n-alkanes (carbon number 10 to 13) or long-chain fatty acids ($C_{10}-C_{18}$) and separating thus grown cells and disrupting the same. The inventors also have succeeded in obtaining a highly purified enzyme itself from thus obtained crude extract by using the techniques of, for example, heat treatment, fractionation with ammonium sulfate, ion-exchanger, gel filtration or the like, and have thus arrived at the invention.

This invention, thus, provides a novel acyl-CoA oxidase which is produced by microorganism and which has the following properties:

(1) Activity

The enzyme is able to act on acyl-CoA in the presence of oxygen to form enoyl-CoA and hydrogen peroxide.

(2) Substrate specificity

The substrate is acyl-CoA whose acyl moiety has 6 to 22 carbon atoms.

(3) pH

The optimum pH is 6.5-9.0 and stabilizing pH is 7.0-8.5.

The present invention provides, in another aspect, a method of producing acyl-CoA oxidase comprising cultivating an acyl-CoA oxidase-producing microorganism belonging to the genus Candida in a nutrient medium, thereby accumulating an amount of acyl-CoA oxidase in yeast cells, and recovering the enzyme from said cells.

The enzyme according to the present invention can catalyze the reaction of long-chain acyl-CoA ($C_6-C_{22}$) with oxygen to give enoyl-CoA and hydrogen peroxide, as shown below:

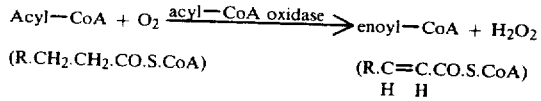

$$\text{Acyl—CoA} + O_2 \xrightarrow{\text{acyl—CoA oxidase}} \text{enoyl—CoA} + H_2O_2$$

$(R.CH_2.CH_2.CO.S.CoA)$      $(R.C{=}C.CO.S.CoA)$
                                                                            H   H

R: alkyl having 3 to 19 carbon atoms

This enzyme is, differing from acyl-CoA dehydrogenase (ECl 1.3.99.3), not active, in the absence of oxygen, to the reduction of cytochrome C in the presence of PMS (phenazine methosulfate) or to the electron transport system to 2,6-DCPIP (dichlorophenolindophenol) and the like. However, when reacted in the presence of oxygen, this enzyme is active, even in the absence of electron transport system, to substrate and it is possible to detect hydrogen peroxide produced. Furthermore, in an oxygen electrode method, the addition of substrate acyl-CoA to the reaction system with the present enzyme apparently causes the decrease in $O_2$ partial pressure, but recovers $O_2$ partial pressure up to ½ of said decrease by the addition of excess amount of catalase. This may apparently be due to the fact that said catalase acts on hydrogen peroxide generated by the action of acyl-CoA oxidase thereby forming one molecule of oxygen from 2 molecules of said hydrogen peroxide. Thus generated hydrogen peroxide may be identified with other colorimetric methods. For example, it is possible to convert thus produced hydrogen peroxide, by the action of catalase and alcohol, to an aldehyde and measure the latter colorimetrically. Alternatively, the produced hydrogen peroxide may be treated, in the presence of color forming agent of 4- aminoantipyrin and phenol, with peroxidase and the developed color may be measured for the determination of said substance.

Figure 3:
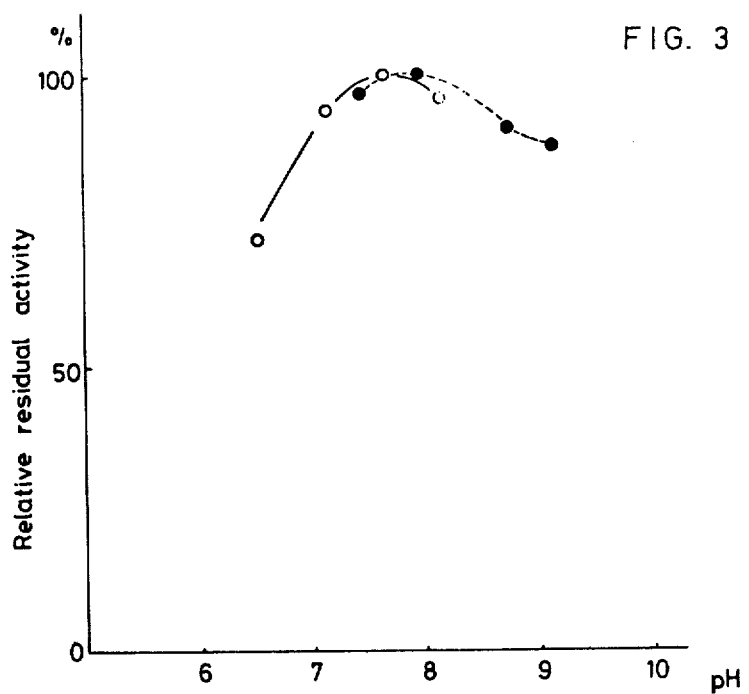
Figure 4:
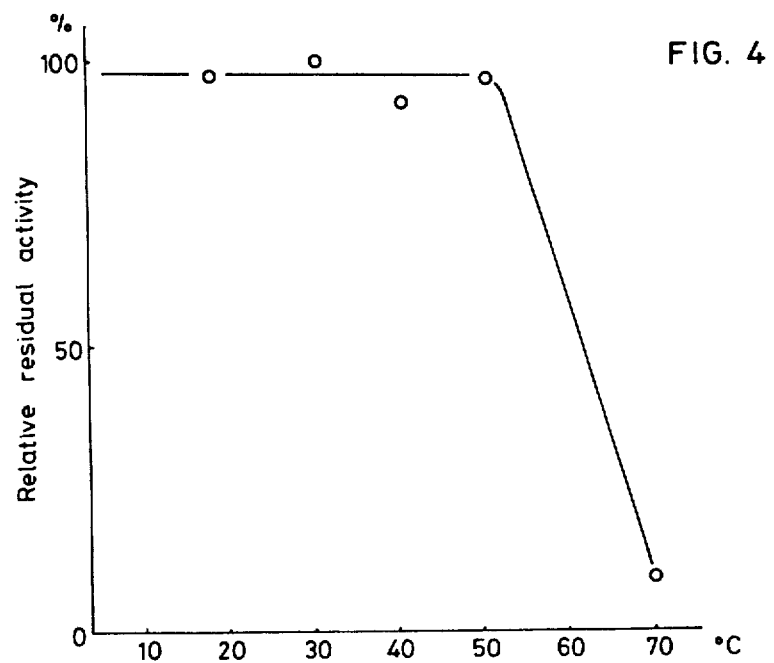
Figure 5:
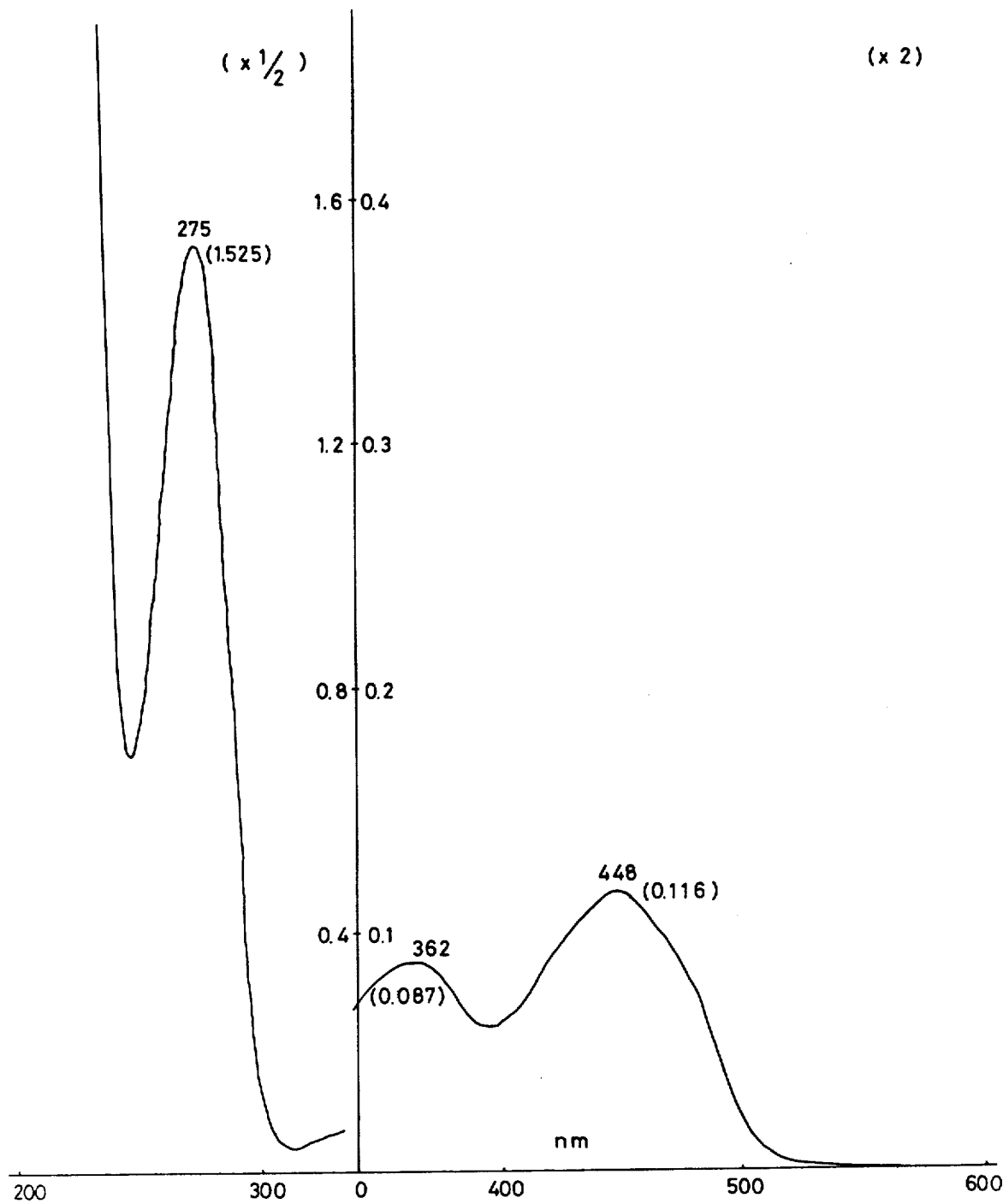

The invention will be further explained below by referring partly to the accompanying drawings wherein FIGS. 1 to 4 are graphs showing optimum pH, optimum temperature, pH stability and heat stability, respectively, of the enzyme of this invention, and FIG. 5 is the absorption spectrum of the enzyme.

Figure 2:
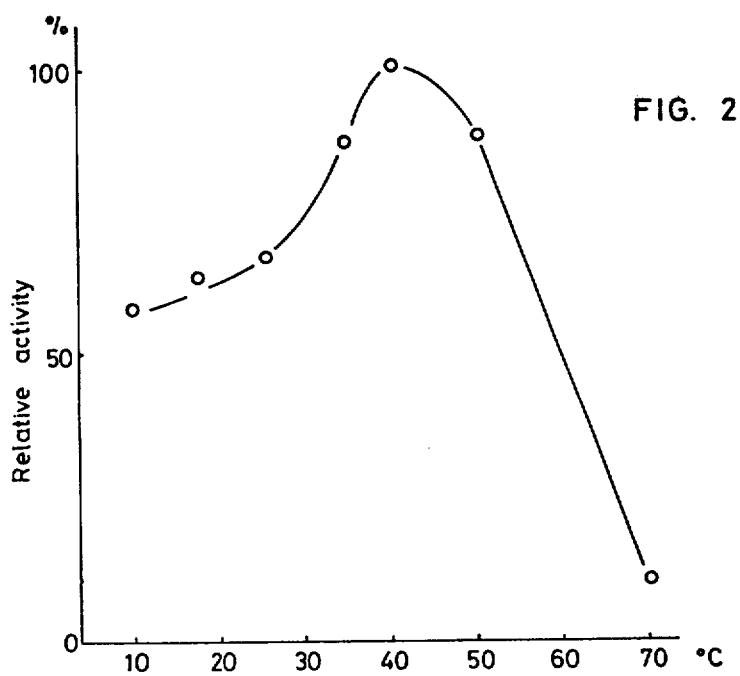

The characteristic properties of the present enzyme are as follows:

The optimum pH is, as shown in FIG. 1, relatively wide, ranging from 6.5 to 9.0, the best range being from 7.3 to 8.0 (in 50 mM potassium phosphate (K-PO$_4$) buffer). The optimum temperature is, as shown in FIG. 2, at around 40° C. This enzyme is, as shown in FIG. 3, stable under pH 7.0-8.5, and, as shown in FIG. 4, is stable up to 50° C. Incidentally, the abovesaid optimum pH was determined in 50 mM K-PO$_4$ buffer and the optimum temperature was in 50 mM K-PO$_4$ buffer (pH 7.5) with the reaction time of 15 minutes. The pH stability was determined after allowing to stand a solution in 50 mM K-PO$_4$ buffer (mark o-o in FIG. 3) or a solution in 50 mM glycin-potassium hydroxide buffer (mark •-• in FIG. 3) at 4° C. for 20 hours, and the heat stability was measured by treating a solution in 50 mM K-PO$_4$ buffer (pH 7.5) for 15 minutes.

The substrate specificity of the present enzyme produced by microorganism belonging to the genus Candida is as shown in the following Table 1.

TABLE 1

| Acyl—CoA (carbon number) | relative activity |
|---|---|
| 6 | 13.0 |
| 8 | 18.5 |
| 10 | 76.1 |
| 12 | 100 |
| 14 | 68.5 |
| 16 | 27.0 |
| 18 | 13.0 |
| 20 | 7.0 |
| 22 | 3.2 |

Molecular weight of the enzyme is about 71,000 (measured by SDS electrophoresis method) and adsorption maximum in absorption spectrum are at around 275 nm, 362 nm and 448 nm. The Km value is about $3.3 \times 10^{-5}$ M.

In the present invention, measurements of enzyme activities were carried out as follows:

Acyl—CoA oxidase activity assay (1):
Reaction mixture:

| 50 mM | KPO$_4$ buffer (pH 7.4) |
|---|---|
| 1 mM | 4-aminoantipyrin |
| 10 mM | phenol |
| 5 μM | FAD (flavinadenin dinucleotide) |
|  | peroxidase  10 U |
| 100 μM | palmityl—CoA |
|  | acyl—CoA oxidase |

1 ml of said reaction mixture is reacted at 37° C. for 15 minutes and thereafter, the increase in absorbance at 550 nm due to the formation of H$_2$O$_2$ is measured. As a unit activity, was used a unit quantity (μ mole) of hydrogen peroxide produced in one minute.

Acyl—CoA oxidase activity assay (2):
Reaction mixture:

| 50 mM | KPO$_4$ buffer (pH 7.8) |
|---|---|
| 5 mM | EDTA 3 Na |
| 4% | methanol |
|  | catalase  800 U/ml |
| 10 μM | BAD (flavinadenindinucleotide) |
| 100 μM | palmityl—CoA |
|  | acyl—CoA oxidase |

0.5 ml of the above said reaction mixture is reacted at 37° C. for 15 minutes to produce formalin and 0.5 ml of 2 N KOH and 0.5 ml of 0.6% AHMT are added thereto. The mixture is allowed to stand for 5 minutes and then added with 1.0 ml of 0.75% NaIO$_4$ to develop color. After 10 minutes, it is subjected to colorimetry at 550 nm absorbance. As a unit of activity, was used a unit quantity (μ mole) of hydrogen peroxide produced in one minute.

In the present invention, any kind of microorganism capable of producing the present enzyme may be satisfactorily used. It is preferable, however, to employ an acyl-CoA producing microorganism belonging to the genus Candida. A method for the production of the present enzyme from acyl-CoA producing microorganism belonging to the genus Candida shall be explained below.

As the acyl-CoA producing microorganism, mention is given of, for example, Candida lipolytica IFO 1548 (ATCC 18942) and Candida tropicalis IFO 0589 (ATCC 20115 and 28142). However, these are only examples of the microorganisms employable in the invention and are not given in limitative sense. In cultivating the above-mentioned microorganism, any of the conventional nutrient media may be used as, for example, alkane medium, glucose medium and the like, and however, preference is given to an alkane medium and especially a medium containing a long-chain fatty acid with 10 to 18 carbon atoms or n-alkane with 10 to 13 carbon atoms. The cultivation may be carried out under usual cultivation conditions.

In obtaining the enzyme from the culture, any method for effecting the elution of said enzyme from the cells may be satisfactorily used as, for example, grinding by means of glass beads, ground quartz or the like, autolysis with toluene, surfactant or cell wall dissolving enzyme and the like and however, preference is given to the mechanical grinding with glass beads.

After disrupting the cells, the cell debris is removed off by appropriate separation means and the cell free extract is then subjected directly or after being condensed, to a purification step of, for example, fractionation by the use of ammonium sulfate, ion-exchange chromatography, gel filtration and the like, optionally with heat treatment, to obtain a highly purified product.

Thus obtained enzyme has the characteristic properties as above-mentioned. The present enzyme is very useful as a reagent in clinical tests, and especially for the determination of free fatty acid. In the latter case, a fatty acid activating enzyme (acyl-CoA synthetase) is first used to act on free fatty acid in the presence of coenzyme A and ATP (adenosine triphosphate) and the produced acyl-coenzyme A is then treated with the present acyl-CoA oxidase in the presence of oxygen, and thus generated hydrogen peroxide is measured for the determination of said free fatty acid. Various potent uses are also expected in other research areas as, for example, in the determination of intermediary metabolites in lipid metabolic system, preparation of said intermediary metabolites and other studies thereon.

The invention shall be explained in detail in the following Examples.

EXAMPLE 1

*Candida lipolytica* IFO 1548 strain was inoculated in 50 ml of the culture medium having the following composition placed in 500 ml Sakaguchi Flask, 1.0% n-alkane ($C_{10}$–$C_{13}$)
0.5% $KH_2PO_4$
0.5% $K_2HPO_4$
0.7% yeast extract
0.7% polypeptone
pH 5.5 and cultivated with shaking for 16 hours at 30° C. Thus obtained seed culture was inoculated to each of 10 flasks of the same medium (each 2 liter flask containing 500 ml of the above-mentioned medium) and cultivated with shaking for an additional 16 hours. The cultured mediums were filtered to collect 80 g (in wet) of cells, which were thoroughly washed with 50 mM K-$PO_4$ buffer (pH 7.5) and then suspended into 400 ml of the same buffer. The suspension was, after being subjected to disrupting with beads, centrifuged to obtain supernatant, which was then subjected to fractionation with ammonium sulfate. This fractionation was carried out at saturation 0.2 to 0.5 and the fraction obtained was redissolved in the same buffer and passed through Sephadex G-25 to remove salts therefrom. After passing through DEAE cellulose, thus obtained solution (50 ml) was treated at 50° C. for 5 minutes, filtered to remove precipitates, concentrated by means of salting-out and subjected to gel filtration using Sephadex G-150 equilibrated with the above-mentioned buffer to obtain a highly purified acyl-CoA oxidase. The activity was 15 units (specific activity 1.2 U/mg of protein) and the yield was 50%.

EXAMPLE 2

Using a 20 liter jar fermenter containing 12 l. of the same culture medium as stated in Example 1, *Candida tropicalis* IFO 0589 strain was cultivated as in Example 1. Thus obtained 385 g (in wet) of washed cells were suspended in 1500 ml of 50 mM K-$PO_4$ buffer (pH 7.5) and the suspension was subjected to disrupting and then to centrifugation. The separated supernatant was then subjected to fractionation with ammonium sulfate, heat treatment and gel filtration as in Example 1 to obtain a highly purified acyl-CoA oxidase. The activity was 85 units (specific activity 1.6 U/mg of protein).

What we claim is:

1. A method for the preparation of acyl-coenzyme A oxidase which comprises cultivating an acyl-coenzyme A oxidase-producing microorganism belonging to the genus Candida in a nutrient medium containing a long-chain fatty acid having 10 to 18 carbon atoms, thereby accumulating an amount of acyl-coenzyme A oxidase in yeast cells and recovering the acyl-coenzyme A oxidase from said cells.

2. A method according to claim 1 wherein the acyl-coenzyme A oxidase produced and accumulated in yeast cells is isolated from said cells as soluble acyl-coenzyme A oxidase.

* * * * *